United States Patent [19]

Mackenzie et al.

[11] Patent Number: 5,387,106
[45] Date of Patent: Feb. 7, 1995

[54] SOLID STATE ARTIFICIAL CORNEA AND METHOD FOR UV LASER SCULPTING

[75] Inventors: Brian W. Mackenzie; Walter W. Duley, both of King City; Melih Ogmen, Mississauga, all of Canada

[73] Assignee: Powerlasers Ltd., Ontario, Canada

[21] Appl. No.: 864,257

[22] Filed: Apr. 6, 1992

[51] Int. Cl.⁶ .................................................. G09B 23/28
[52] U.S. Cl. ........................................ 434/271; 434/267
[58] Field of Search ............... 434/271, 270, 267, 262; 356/152, 121; 606/5, 4, 11, 10, 2

[56] References Cited

U.S. PATENT DOCUMENTS

| | | | |
|---|---|---|---|
| 4,601,037 | 7/1986 | McDonald | 606/11 X |
| 4,692,924 | 9/1987 | Koizumi et al. | 606/11 X |
| 5,049,147 | 9/1991 | Danon | 606/11 X |
| 5,066,294 | 11/1991 | Cosmescu | 606/11 |
| 5,067,811 | 11/1991 | Ouchi | 356/121 |
| 5,078,491 | 1/1992 | Johnston | 356/121 |
| 5,090,798 | 2/1992 | Kohayakawa | 606/5 X |
| 5,098,426 | 3/1992 | Sklar | 606/10 X |

FOREIGN PATENT DOCUMENTS

| | | | |
|---|---|---|---|
| 2832847 | 2/1980 | Germany | 606/11 |
| 2141225 | 12/1984 | United Kingdom | 606/4 |

OTHER PUBLICATIONS

"Excimer Laser Surgery Of The Cornea" by Stephen L. Trokel, MD, R. Srinivasan, Ph.D., and Bodil Braren, B. A., *American Journal of Ophthalmology*, 1983, pp. 710–715.

"Effect of Excimer Laser on Microbiological Organisms" by Richard H. Keates, M.D., Paul C. Drago, B.S., and Eric J. Rothchild, M.D., *Ophthalmic Surgery*, Oct. 1988, vol. 19, No. 10, pp. 715–718.

"Loss of Human Photoreceptor Sensitivity Associated with Chronic Exposure to Ultraviolet Radiation" by John S. Werner, Ph.D., Victoria G. Steele, MA, and David S. Pfoff, MD, *Ophthalmology*, Oct. 1989, vol. 96, No. 10, pp. 1552–1558.

"Excimer Laser Ablation of the Cornea and Lens"–Experimental Studies, by Carmen A. Puliafito, MD, Roger F. Steinert, MD, Thomas F. Deutsch, Ph.D., Franz Hillenkamp, Ph.D., Ellen J. Dehm, BA, Catherine M. Adler, BS, HT (ASCP), *Ophthalmology*, Jun. 1985, vol. 92, No. 6, pp. 741–748.

"Interaction of Ultraviolet Laser Light With the Cornea" by Ronald R. Krueger, Stephen L. Trokel, and Hermann D. Schubert, *Investigative Ophthalmology & Visual Science*, Nov. 1985, vol. 26/11, pp. 1455–1464.

"Excimer Laser Keratectomy for Myopia With a Rotating-Slit Delivery System" by Khalil D. Hanna, MD, J. C. Chastang; Yves Pouliquen, MD, Gilles Renard, MD, Louis Asfar, George O. Waring, III, MD, *Arch Ophthalmol*, Feb. 1988, vol. 106, pp. 245–250.

"Excimer Laser Keratoplasty Part 2: Elliptical Keratoplasty" by Gerhard K. Lang, MD, Eckhard Schroeder, Ph.D., Juergen W. Koch, MD, Myron Yanoff, MD, Gottfried O. H. Naumann, MD, *Ophthalmic Surgery*, May 1989, vol. 20, No. 5, pp. 342–346.

"Ultraviolet Light Exposure and Risk of Posterior Subcapsular Cataracts" by Tom W. Bochow, MD, MPH, Sheila K. West, Ph.D., Alex Azar, MD, Beatriz Munoz, MS, Alfred Sommer, MD, MHSc, Hugh R. Taylor, MD, *Arch Ophthalmol*, Mar. 1989, vol. 107, pp. 369–372.

"Corneal Repair following Keratectomy"–A Comparison between Conventional Surgery and Laser Photoablation by Stephen J. Tuff, Ralph W. Zabel, and John (List continued on next page.)

Primary Examiner—John J. Wilson
Assistant Examiner—Jeffrey A. Smith
Attorney, Agent, or Firm—Staas & Halsey

[57] ABSTRACT

An artificial cornea for sensing and integrating UV radiation in real time. The cornea includes an EPROM array adapted to be exposed to UV radiation. Individual bits of the EPROM array are set prior to being exposed to the UV radiation. In response to being exposed to the UV radiation predetermined ones of the individual bits are erased. Means for monitoring, in real time, the locations of the predetermined erased bits are provided and, in response, a record is formed of the energy distribution of the UV radiation across the EPROM array.

4 Claims, 12 Drawing Sheets

OTHER PUBLICATIONS

Marshall, *Investigative Ophthalmology & Visual Science,* Aug. 1989, vol. 30, pp. 1769–1777.

"Dynamics of the Ultraviolet Laser Ablation of Corneal Tissue" by R. Srinivasan, Ph.D. and E. Sutcliffe, Ph.D., *American Journal of Ophthalmology,* vol. 103, No. 3, Part II, pp. 470–471.

"Refractive Surgery With the Excimer Laser" by Marguerite B. McDonald, M.D., Roger Beuerman, Ph.D., Wendy Falzoni, M.D., Lilia Rivera, M.D., and H. E. Kaufman, MD, *American Journal of Ophthalmology,* vol. 103, No. 3, Part II, p. 469.

"Excimer Laser Cut Lenticules for Epikeratophakia" by Richard C. Lieurance, MD, Arun C. Patel, MD, W. Lee, Wan, MD, Richard F. Beatty, MD, Roger L. Kash, AA, and David J. Schanzlin, MD, *American Journal of Ophthalmology,* vol. 103, No. 3, Part II, pp. 475–476.

"A Refractive and Histopathologic Study of Excimer Laser Keratectomy in Primates" by Robert A. Del Pero, MD, Joan E. Gigstad, MD, Alfred D. Roberts, MD, Gordon K. Klintworth, MD, Clifford A. Martin, Ph.D., Francis A. L'Esperance, Jr., MD, and Daniel M. Taylor, MD, *American Journal of Ophthalmology,* Apr. 1990, vol. 109, No. 4, pp. 419–429.

"An Ultrastructural Study of Corneal Incisions Induced by an Excimer Laser at 193 nm" by John Marshall, Ph.D., Stephen Trokel, MD, Stephen Rothery, BSc, Hermann Schubert, MD, *Ophthalmology,* Jun. 1985, vol. 92, No. 6, pp. 749–758.

"High Speed Photography of Excimer Laser Ablation of the Cornea" Carmen A. Puliafito, MD, David Stern, MS, Ronald R. Krueger, MD, Eric R. Mandel, MD, *Arch Ophthalmol,* Sep. 1987, vol. 105, pp. 1255–1259.

"Host Factors, UV Radiation, and Risk of Uveal Melanoma"–A Case-Control Study, by Johanna M. Seddon, MD, Evangelos S. Gragoudas, MD, Robert J. Glynn, SeD, Kathleen M. Egan, MPH, Daniel M. Albert, MD, and Peter H. Blitzer, MD, *Arch Ophthalmol,* Sep. 1990, vol. 108, pp. 1274–1280.

"Corneal Changes Associated With Chronic UV Irradiation" by Hugh R. Taylor, MD, Sheila K. West, Ph.D., Franks S. Rosenthal, Ph.D., Beatriz Munoz, MS, Henry S. Newland, FRACS, Edward A. Emmett, MD, *Arch Ophthalmol,* vol. 107, Oct. 1989, pp. 1481–1484.

"Eye Surgeons Pursue Corneal Sculpting By Laser" by Michael Moretti, *News/Lasers and Optics,* pp. 28, 30 & 32.

"Immunofluorescence Study of Corneal Wound Healing After Excimer Laser Anterior Keratectomy in the Monkey Eye" by Debra S. Malley, Roger F. Steinert, MD, Carmen A. Puliafito, MD, Ernest T. Dobi, Ph.D., *Arch Ophthalmol,* vol. 108, Sep. 1990, pp. 1316–1322.

"A Rotating Slit Delivery System for Excimer Laser Refractive Keratoplasty" by Khalil Hanna, MD, J. C. Chastang, Yves Pouliquen, MD, Gilles Renard, MD, Louis Asfar and George O. Waring III, MD, *American Journal of Ophthalmology,* Mar. 1987, p. 474.

"An Ophthalmic Excimer Laser for Corneal Surgery" by E. Schröder, Ph.D., M. U. Dardenne, MD, T. Neuhann, MD, and A. Tenner, MD, *American Journal of Ophthalmology,* Mar. 1987, pp. 472–473.

"Photodamage to Calf Lenses In Vitro by Excimer Laser Radiation at 308, 327, and 350 nm" by Dong-yun Li and Raymond F. Barkman, *Investigative Ophthalmology & Visual Science,* vol. 31, No. 10, Oct. 1990, pp. 2180–2184.

"Excimer Laser Keratoplasty Part 1: Basic Concepts" by Gerhard K. Lang, MD, Eckhard Schroeder, Ph.D., Juergen W. Koch, MD, Myron Yanoff, MD, and Gottfried O. H. Naumann, MD, *Ophthalmology Surgery,* Apr. 1989, vol. 20, No. 4, pp. 262–267.

"Wound Healing After Excimer Laser Keratomileusis (Photorefractive Keratectomy) in Monkeys" by Francisco E. Fantes, MD, Khalil D. Hanna, MD, George O. Waring III, MD, Yves Pouliquen, MD, Keith P. Thompson, MD, Michelle Savoldelli, *Arch Ophthalmol,* vol. 108, May 1990, pp. 665–675.

"Excimer Laser Keratectomy for Correction of Astigmatism" by Theo Seiler, MD, T. Bende, Ph.D., J. Wollensak, MD, and Stephen Trokel, MD, *American Journal of Ophthalmology,* vol. 105, No. 2, Feb. 1988, pp. 117–124.

"Excimer Laser Radial keratotomy" by Arthur M. Cotliar, MD, Hermann D. Schubert, MD, Eric R. Mandel, MD, and Stephen L. Trodel, MD, *Ophthalmology,* Feb. 1985, vol. 92, No. 2, pp. 206–208.

"Human Excimer Laser Lamellar Refractive Keratectomy" by Taylor et al., *Ophthalmology,* May 1989, vol. 96, No. 5, pp. 660–664.

"Characterization of the Fluorescence Spectra Produced by Excimer Laser Irradation of the Cornea" by Stephen Tuft, Rashid Al-Dhahir, Peter Dyer and Zhu Zehaot, *Investigative Ophthalmology & Visual Sciene,* vol. 31, No. 8, Aug. 1990, pp. 1512–1518.

SOLID STATE ARTIFICIAL CORNEA AND METHOD FOR UV LASER SCULPTING

FIELD OF THE INVENTION

The present invention relates in general to surgical laser systems, and more particularly to a solid state artificial cornea for UV laser corneal sculpting.

BACKGROUND OF THE INVENTION

Corneal keratectomy is a surgical procedure which changes the refractive characteristics of the cornea by making deep incisions on the cornea. The procedure is used to eliminate or reduce eye disorders such as myopia, hyperopia and astigmatism.

Incision depth is the most critical factor in determining the refractive outcome to the keratectomy surgery. Results of the conventional technique are found to be inconsistent due to the use of steel or diamond knives. The corneal incisions have been found to vary considerably from the expected depth, with ranges from 66% to 96% for steel and 61% to 98% for diamond knife incisions.

It was discovered in or about 1981, that the corneal epithelium exhibits an unusual sensitivity to 193 nm laser light. Laser light of this wavelength was shown to be capable of etching organic substrates in or about 1982. It was then shown that this etching effect would similarly occur with biological tissue. More particularly, in 1983, in a series of experiments, (Trokel, S., Srinivasan, R. and Branen, B., Am. J. Opthal. 96:710 (1983)) the corneal stroma was ablated with an accuracy comparable to organic substrates.

The excimer laser is the most convenient source of UV laser light and has 193, 249, 308 and 351 nm light as major emission lines. These wavelengths span the UV spectrum and provide a suitable range with which to examine corneal tissue interactions. These four wavelengths can be produced at sufficiently high irradiance to cause corneal tissue ablation.

Therefore, the technique of UV laser keratectomy, was developed to replace conventional surgical corneal sculpting using diamond knives. The use of excimer lasers for corneal sculpting has proliferated during recent years.

The sharply controlled cutting/ablation ability of excimer lasers contrasts with the less controlled techniques which use the longer wavelength infrared laser frequencies which are also absorbed by corneal tissue. A $CO_2$ laser, emitting light at 10.6 $\mu$m, produces an incision with irregular jagged edges, which chars the collagenous material of stroma (Keates et al 1981). This effect is quite unlike the uniform incisions produces by the 193 nm emission of the excimer laser. Consequently the excimer laser has developed into a preferred apparatus for corneal surgery.

Excimer lasers have been used to perform three types of refractive surgery. The first type uses the laser to create linear or circular excisions of corneal tissue, similar to conventional incision techniques. These incisions are effected to alter the mechanical stress patterns of the incised corneal stroma. In the untouched central cornea a new stress equilibrium is established, which produces a new optical curvature. The second type of refractive surgery involves ablation of surface areas of the cornea to create a new anterior curvature variously known as surface etching, reprofiling, surface ablation, and laser keratomileusis. The third type of refractive surgery involves removing tissue from discs of excised cornea in keratomileusis and epikeratoplasty.

Among numerous parameters that must be defined and controlled for these operations are the uniformity of the laser beam, the amount of radiant exposure, the energy distribution achieved on the cornea, the repetition rate of the laser, the total number of pulses, the total amount of energy delivered, as well as the shape and energy distribution of the laser beam as it impacts the cornea.

The underlying assumption for UV laser keratectomy is that if all of the individual parameters are set satisfactorily the overall result will be accurate. There are over ten parameters relating to this procedure. The above assumption ignores the interdependencies of these parameters. Currently there is no means of checking the overall result of these interdependencies on the actual cornea. For example, changing the intensity distribution of the beam will affect the energy per pulse and the resulting focusing characteristics. This in turn will affect the fluence on the cornea and ablation characteristics. If several of the parameters are readjusted prior to the operation then the overall result on the cornea becomes unpredictable.

The only way to ensure the repeatability of this surgical procedure is by characterizing the overall effect of the procedure on the cornea. A number of different lasers and surgical systems, each with a different number of parameters and optical path characteristics are currently being used. It is impossible to compare the results achieved with these intrinsically different systems.

It is also a well documented fact that excessive UV exposure to the eye causes and contributes to, among other effects, cataracts, uveal melanoma and photoreceptor insensitivity. Therefore, it is very important to determine and record the amount of UV radiation received by the eye during the operation. Currently, this in not being done during UV laser corneal sculpting surgery. Success of the operation is always judged after the operation.

SUMMARY OF THE INVENTION

According to the present invention, a system is provided for enabling surgeons to predict the results of UV laser refractive surgery before the surgery is actually performed on the patient.

The principle of the invention can be summarized as follows. After setting the above mentioned parameters, the surgeon performs the operation on a solid state artificial cornea. The artificial cornea displays the total energy distribution, in real time, as it would occur on the cornea during and after the surgery. Energy deposited on the corneal surface is directly related to the amount of material removed from the cornea. Thus the artificial cornea of the present invention allows the surgeon to determine how much ablation has occurred and where it preferentially has occurred. The surgeon can then decide if the distribution is satisfactory to achieve the maximum dioptre correction. If not, system parameters can be readjusted and the artificial cornea used again until the surgeon is satisfied with the results. Then, the surgery can be performed on the patient with confidence of an optimized response.

The artificial cornea of the present invention increases the safety and reliability of laser corneal sculpting, and allows comparison of the results independent of the laser and other parameters.

Furthermore, the artificial cornea of this invention allows surgeons to record the exact details of UV exposure during the surgery. The record is nonvolatile and permanent. Therefore, if further treatment is necessary in the future the surgeon will have an exact record of what had been previously done. Such a capability will also provide the means to perform accurate comparative studies of possible long term effects.

The system of the present invention can also be used for determining the energy profile of a laser beam prior to the operation. Laser power, transverse modes and energy density distribution are key parameters for characterization of the laser beam. The energy density distribution determines the quality of the etch pattern produced on the cornea. Currently this information is obtained by pyroelectric or calorimetric techniques. The required instrumentation is highly complicated and demands electronics expertise. The artificial cornea of the present invention produces the same information. This reduces the proliferation of complicated electronic equipment necessary for the surgery and allows the surgeon to focus on the task at hand.

In general, the present invention comprises an artificial cornea in the form of a solid state device which interacts with UV lasers where this interaction causes a distinctive and nonvolatile change of state in the device. The solid state components of the device are designed to be robust enough to withstand the laser pulse impact.

The UV sensitivity of the artificial cornea is tailored to match the human cornea's interaction with UV light. Means are also provided to control the sensitivity of the device to UV light.

Furthermore, according to the present invention, sophisticated graphic software may be provided to interface with the surgeon. The software allows the surgeon to assess the surgical data quickly and with minimal distractions.

BRIEF DESCRIPTION OF THE DRAWINGS

A description of the preferred embodiment of the present invention is provided herein below with reference to the following drawings, in which.

DETAILED DESCRIPTION OF THE PREFERRED EMBODIMENT

As discussed above, three techniques have evolved for the clinical use of excimer lasers for refractive surgery of the cornea. One approach uses the laser to create linear or circular excisions of corneal tissue, similar to conventional incision techniques. These incisions are made to alter the mechanical stress patterns of the incised cornea stroma. In the untouched central cornea a new stress equilibrium is established which produces a new optical curve.

Incisions are produced either by imaging with a slit located very near the cornea or by using an aperture and cylindrical lens. Various laser parameters for the radial keratectomy technique are summarized below in Table 1. Generally unstable resonators are used to reduce the beam divergence. The complete procedure takes about 15 minutes. The excimer exposure time for each excision in usually under 40 seconds. The total fluence of 1 joule/$cm^2$ on the cornea ablates a depth of approximately 1 μm.

TABLE 1

| Wavelength (nm) | Energy per Pulse (mj) | Frequency (Hz) | Fluence on Cornea mj/$cm^2$/pulse | Etch depth Per Pulse (μm) | Reference |
|---|---|---|---|---|---|
| 193 | 80 | 10 | | threshold | Marshall 1985 |
| 193 | 100–250 | 1 | 50 | threshold | Krueger 1985 |
| 249 | 100–250 | 1 | 185 | threshold | Krueger 1985 |
| 308 | 100–250 | 1 | 540 | threshold | Krueger 1985 |
| 351 | 100–250 | 1 | 1050 | threshold | Krueger 1985 |
| 193 | 100–250 | 10 | 50 | threshold | Krueger 1985 |
| 249 | 100–250 | 10 | 120 | threshold | Krueger 1985 |
| 308 | 100–250 | 10 | 500 | threshold | Krueger 1985 |
| 351 | 100–250 | 10 | 1000 | threshold | Krueger 1985 |
| 193 | 100–250 | 25 | 55 | threshold | Krueger 1985 |
| 249 | 100–250 | 25 | 80 | threshold | Krueger 1985 |
| 308 | 100–250 | 25 | 420 | threshold | Krueger 1985 |
| 351 | 100–250 | 25 | 900 | threshold | Krueger 1985 |
| 193 | 100 | 10 | | | Cotliar 1985 |
| 193 | | 1–20 | 100–200 | | Trokel 1982 |
| 193 | 30 | | 165 | | Seiler 1988 |

The second approach directly affects the optical center of the cornea where ablation of tissue from the central region defines a new refractive surface.

Figure 1:
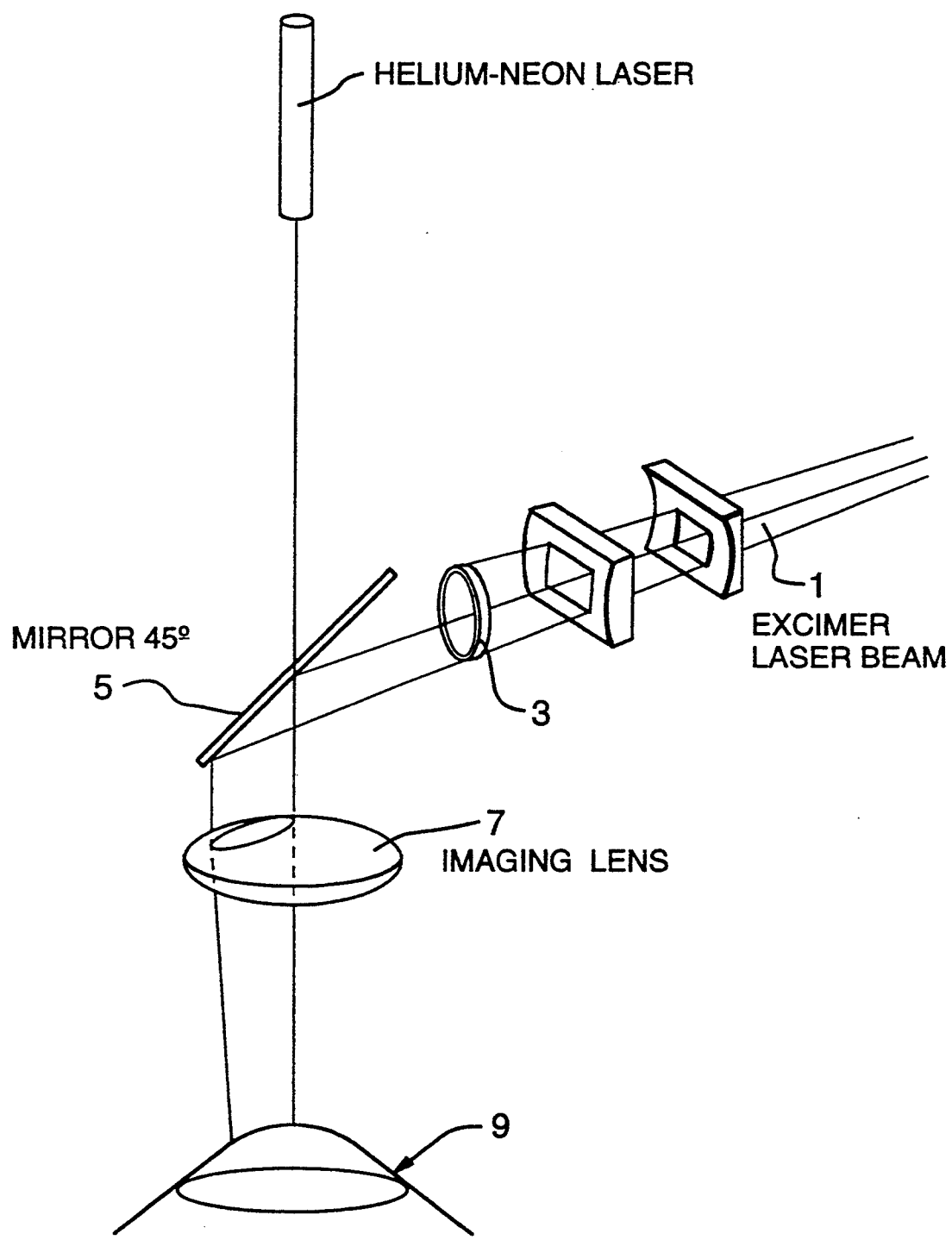
FIG. 1 is a schematic representation of a rotating slit UV surgical laser according to the prior art.

FIG. 1 illustrates a surgical arrangement of effecting UV laser corneal ablation according to this second technique.

The arrangement comprises a novel laser beam delivery system which produces a nonuniform, smooth surface ablation of the cornea. The laser beam 1 illuminates a rotating disk 3 which contains a single radial slit extending out from the center in the shape of a feather (i.e. widest at the middle). The shape of the slit is determined mathematically to perform a parabolic profile of correction for myopia that results from the slit rotation. The pulsed beam is reflected off of a mirror 5 and then focused via lens 7 onto the corneal surface of the eye 9. The ablation takes its maximal value at the center on the visual axis and its minimal value (zero) at the periphery of the carved zone.

Conceptually, the ablation profile is a function of the initial radius of curvature of the cornea. To correct myopia the ablation profile should vary from maximum at the centre of the cornea to minimum at the edge, hence decreasing the corneal curvature and refractive power at that area. The total amount of tissue ablated is a function of laser energy fluence, total area of the rotating slit 3, the angular rotational velocity of the slit and the repetition rate of the laser.

Many other types of delivery systems have also been designed to project a desired configuration of the laser onto the surface of the cornea. These include masks and diaphragms (discussed in greater detail below with reference to FIG. 2), as well as slit shapes.

To correctly characterize a UV laser keratectomy operation, all of the above mentioned variables along with various other laser and optical path related variables have to be strictly defined and recorded. Such proliferation of parameters makes it very difficult to replicate and compare the results of operations performed at different dates and locations. If the total energy density deposited on the cornea is recorded along with the number of pulses the characterization process becomes simple, reliable and repeatable. The artificial cornea of the present invention is designed to facilitate such a simplification.

Table 2 summarizes laser parameters for the keratectomy operation.

TABLE 2

| Wavelength (nm) | Energy per Pulse (mj) | Frequency (Hz) | Fluence on Cornea mj/cm²/pulse | Etch depth Per Pulse (μm) | Reference |
| --- | --- | --- | --- | --- | --- |
| 193 | 167 | 20 | 200 | 0.17 | Hanna 1988 |
| 193 | 200 | 10 | 85–100 | 0.1–0.3 | Del Pero 1990 |
| 193 | 160 | 5 | 250 | 0.45 | Fantes 1990 |
| 193 | 200 | 10 | 85–100 | 0.1–0.3 | Taylor 1989 |

The third method involves noncontact trephination of recipient and donor corneas for the epikeratoplasty operation. Since the first successful keratoplasty, performed by E. Zirm in 1906, the basic surgical technique has not changed. Despite advantages in manual and motorized mechanical trephine design, high and irregular astigmatism still is a major factor limiting the functional results of penetration keratoplasty.

An important consideration for the keratoplasty operation is the effect of external pressure on the resultant trephine cut. Because of the lamellar structure of the cornea, every mechanical trephination necessarily requires pressure. This pressure causes both a torsion of the tissue in the cutting direction and the lateral deviation of the cut, creating a curved cut edge in cross section.

Excimer laser trephination is a non contact procedure. Therefore, cut deviation is totally eliminated. The direction of the corneal incision depends on the angle of incidence of the UV laser. Depending on the type of mask utilized it is possible to produce circular or elliptical buttons.

Figure 2:
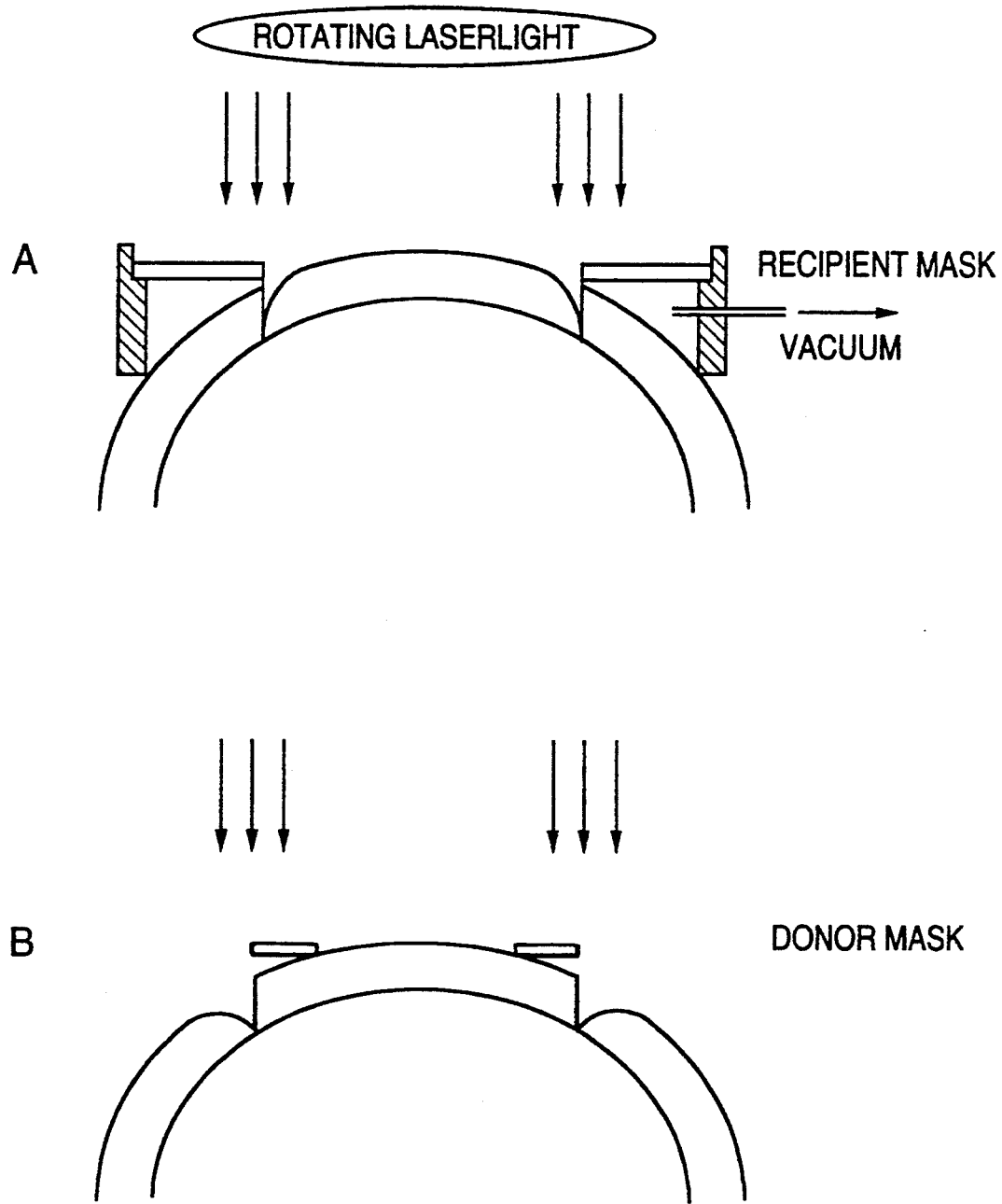
FIG. 2 is a schematic cross section of a recipient mask device (A) and donor mask (B) for use in laser corneal surgery according to the prior art.

FIG. 2 illustrates the use of donor masks and recipient masks according to this prior art technique.

The laser parameters for this surgical procedure are as follows: wavelength 193 nm, frequency 30 Hz, and fluence at the cornea 700 mj/cm². The exposure time varies between three and four minutes for a 8 mm circular trephination.

The excimar laser has a great potential for clincal application in corneal surgery. The corneal stroma, which is composed primarily of an extracellular matrix with few cells and with no blood vessels is an excellent biological target for UV ablation. To establish this technique among other standard techniques, reliable long term studies are necessary. A permanent and accurate record of the corneal ablation process provides the means for such a study.

According to a broad aspect of the present invention an artificial cornea is provided for sensing and integrating exposure to UV radiation and creating a permanent record of such exposure. The sensing and integrating may be effected by various means such as UV curable resins, recording UV phosphorescence via CCD camera, etc. According to the preferred embodiment, an EPROM like array of MOS transistors are arranged to form an articial cornea for measuring and integrating UV radiation in real time.

Figure 3:
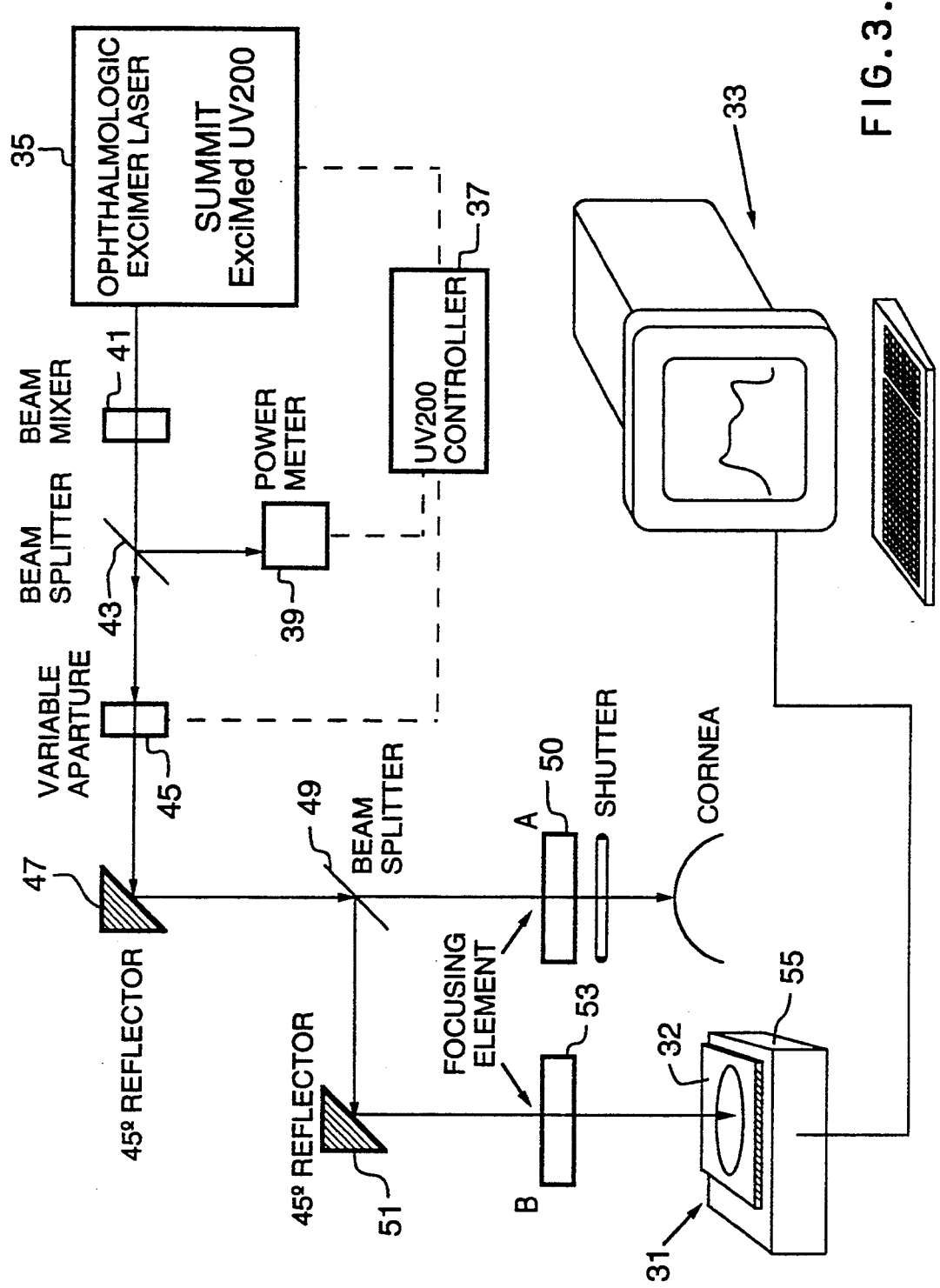
FIG. 3 is a block diagram of an artificial cornea and test system therefor, in accordance with the preferred embodiment.

With reference to FIG. 3, an artificial cornea 31 is shown connected to a computer 33 for sensing and measuring UV radiation from an opthalmologic excimer laser 35 (e.g. ExciMed UV200 TM excimer laser manufactured by Summit) controlled by an excimer laser controller 37 (e.g. Summit UV200 Controller) in conjuction with a power meter 39. The laser 35, controller 37 and power meter 39 are of standard design and construction and the operation and construction thereof would be well known to a person skilled in the art.

Collimated laser light output from excimer laser 35 is optically processed via a beam mixer 41, beam splitter 43 and variable aperture 45, in a well known manner. The processed beam is then reflected via a mirror 47 and split into two beams via a further beam splitter 49. One of the split beams passes through a first focusing element 50 while the other beam is reflected off of a mirror 51 and passes through a second focusing element 53 (e.g. lens). The first split beam then passes through a shutter (e.g. such as the rotating disc 3 in FIG. 1) for application to a human cornea. The second split beam is focused onto the artificial cornea 31 for sensing and recording UV radiation.

As discussed in greater detail below, the artificial cornea preferably comprises an EPROM array 32 of MOS transistors 11 each of which is set prior to irradiation with UV light, and respective ones of which are erased in response to being irradiated.

The EPROM array 32 is connected to a controller-/interface device 55 for reading and writing data into the array 32. The device 55 is connected to a peripheral port of computer 33 for effecting communication therebetween. In particular, computer 33 generates signals for setting all transistors 11 (FIG. 4) prior to irradiation. The artificial cornea 31 is then irradiated such that predetermined cells or MOS transistors thereof are erased, as discussed in greater detail below with reference to FIGS. 4–7). The computer 33 then reads the locations of EPROM array 32 and creates an irradiation profile or record in two-dimensions and three-dimensions, as shown in FIGS. 8 and 9). Any suitable data acquisition and graphics software may be used to create the irradiation record. For example, at the time of filing this application, computer 33 executed the Graftool TM graphical analysis system by 3D Visions Corporation for generating the profiles shown in FIGS. 8 and 9.

Figure 4:
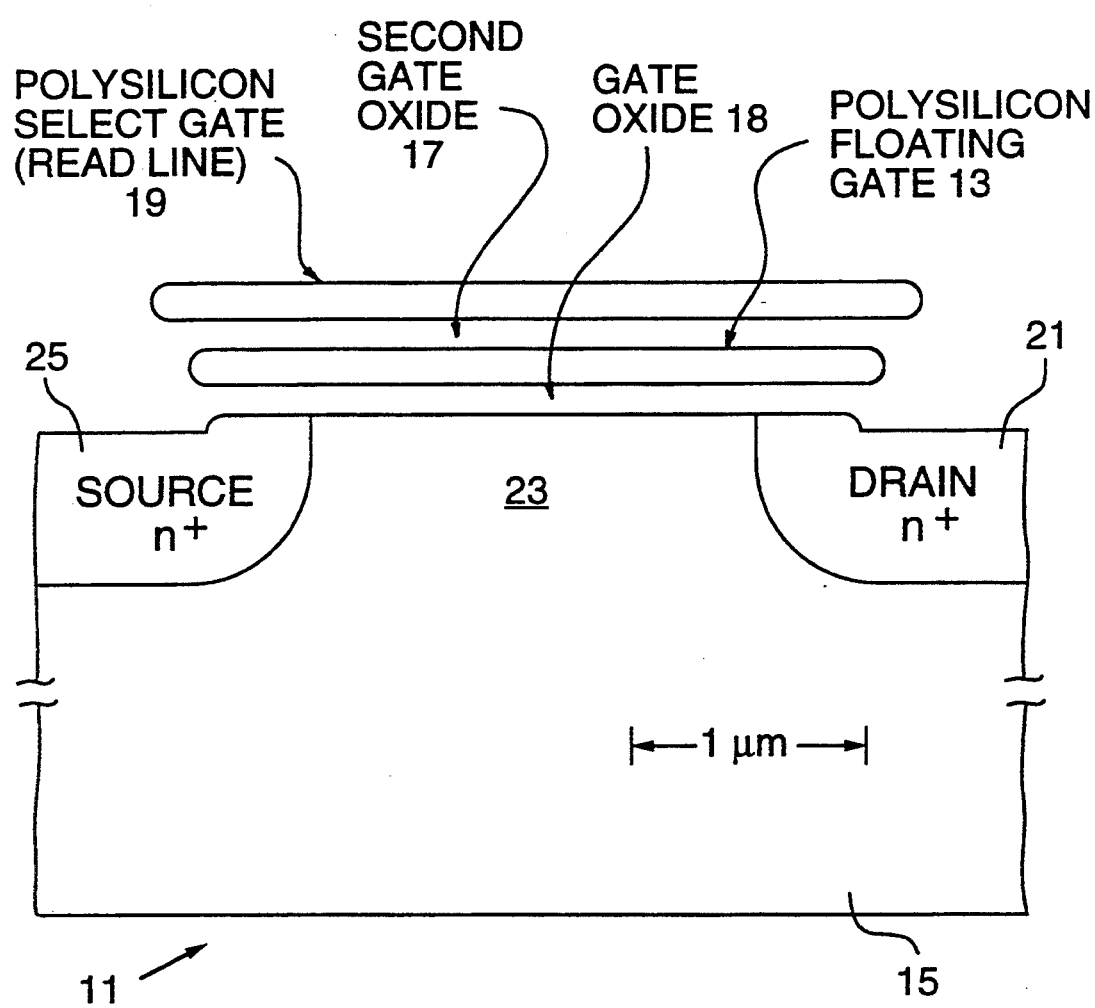
FIG. 4 is a schematic cross sectional view of a standard MOS transistor forming an EPROM cell adapted for use in the artificial cornea of FIG. 3.

Turning to FIG. 4, a MOS transistor 11 is shown with the addition of a floating gate 13 buried in the insulator 17, 18 between the substrate 15 and the select gate electrode 19. As a result, the select gate voltage is capacitively coupled in series with the floating gate rather than directly to the underlying channel. Charge stored on the floating gate 13 alters the threshold voltage of the device 11 as detected at the top of the select gate 19.

Figure 5A:
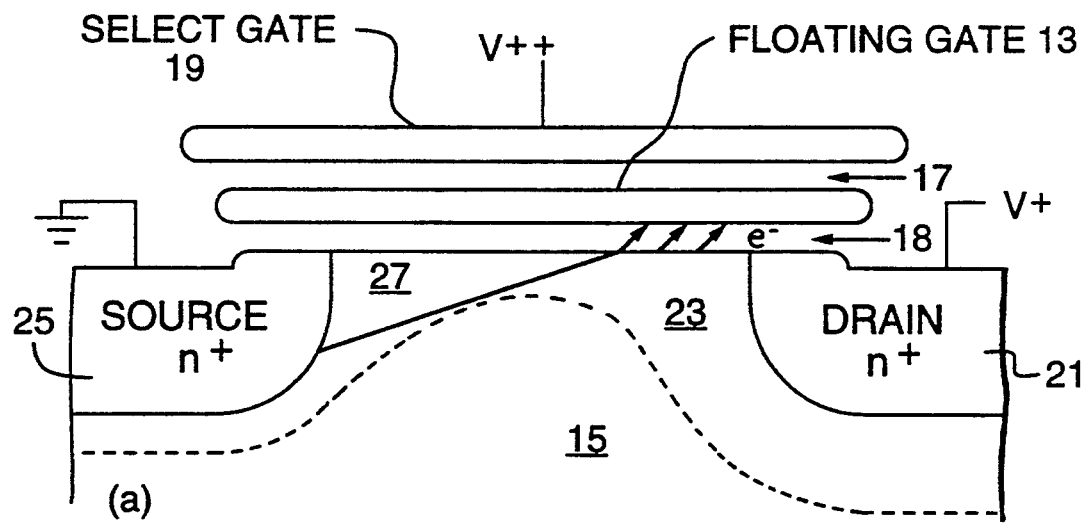
FIGS. 5(a) and (b) are schematic cross sections of the standard MOS transistor cell of FIG. 4 showing electron flow during programming of the cell (a), and during erasure (b)
Figure 5B:
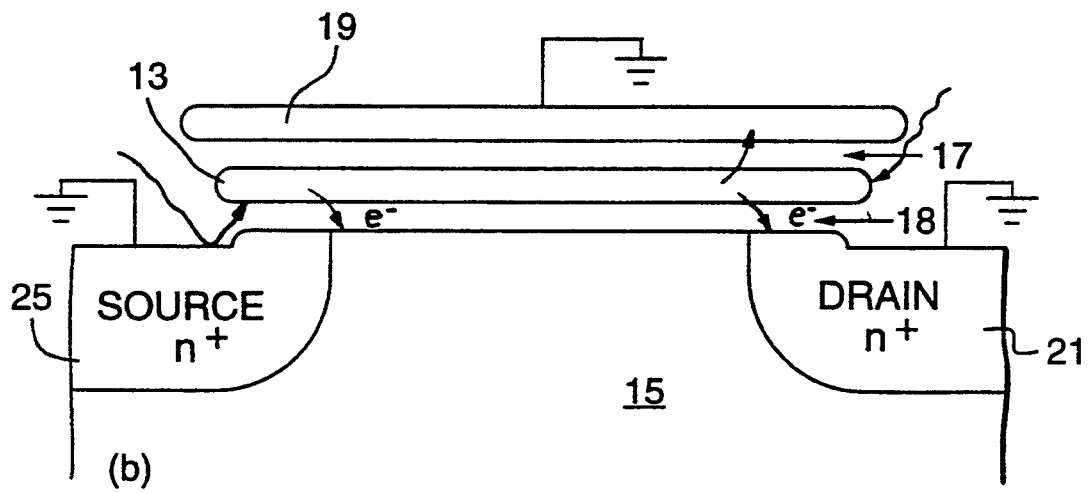

The cell is programmed by charging the floating gate 13 via the injection of so-called hot electrons from the drain pinch-off region (FIG. 5(a)).

The cell is erased through internal photoemission from the floating gate 13 to the top gate 19 and substrate 15. Ultraviolet light gives electrons on the floating gate 13 enough energy to surmount the energy barrier between the floating gate and the insulator 17, 18 surrounding it.

The charge on the cell floating gate 13 changes the threshold voltage of the select gate 19 by an amount $$\Delta V_t = -\frac{\Delta Q_{FG}}{C}$$

where C is the capacitance between the floating gate 13 and the select gate 19 and $\Delta Q_{FG}$ is the change in charge on the floating gate. When the cell 11 is programmed, the negative charge on the floating gate 13 causes the floating gate-to-source voltage to be negative. This turns the cell 11 off, even with a positive voltage applied to gate 19.

Since the floating gate 13 is not tied to a power supply, its voltage is determined by its charge and by capacitance coupling to the voltages of the select gate 19, the drain 21, the channel 23 and source 25.

The hot electrons get their energy from the voltage applied to the drain 21 of the cell 11. They are accelerated along the channel 23 into the even higher fields surrounding the drain depletion region (FIG. 5(a)). While traversing the channel 23, the electrons enter a region where the electron field in the substrate 15 is about $10^5$v/cm greater. At this point the rate of energy gained from the electric field can no longer be described by the temperature of the silicon; hence the term "Hot". Once these electrons gain sufficient energy they can surmount the energy barrier between the silicon substrate 15 and the silicon dioxide insulator 18. Because energy loss due to phonon emission increases at higher lattice temperatures, it is actually easier to obtain hot electrons at lower operating temperatures.

In addition to phonon emission, hot electrons may give up some of this energy in another way: through electron-hole pair creation resulting from impact ionization. This phenomenon is observed in ordinary MOS transistors as a result of the onset of substrate current at high drain voltages. However, in the embodiment of the present invention, significant current multiplication produces substantial substrate current even before a large enough drain voltage is reached to produce hot-electron injection into the oxide 18.

With positive drain and channel voltages, electrons injected into the oxide layer 18 return to the substrate 15 unless a high positive select-gate voltage is applied to pull the electrons toward the floating gate 13. Not only does the floating gate have to be positively biased with respect to the source, it must also be positive with respect to the point along the channel 23 where hot electron injection occurs.

Figure 6:
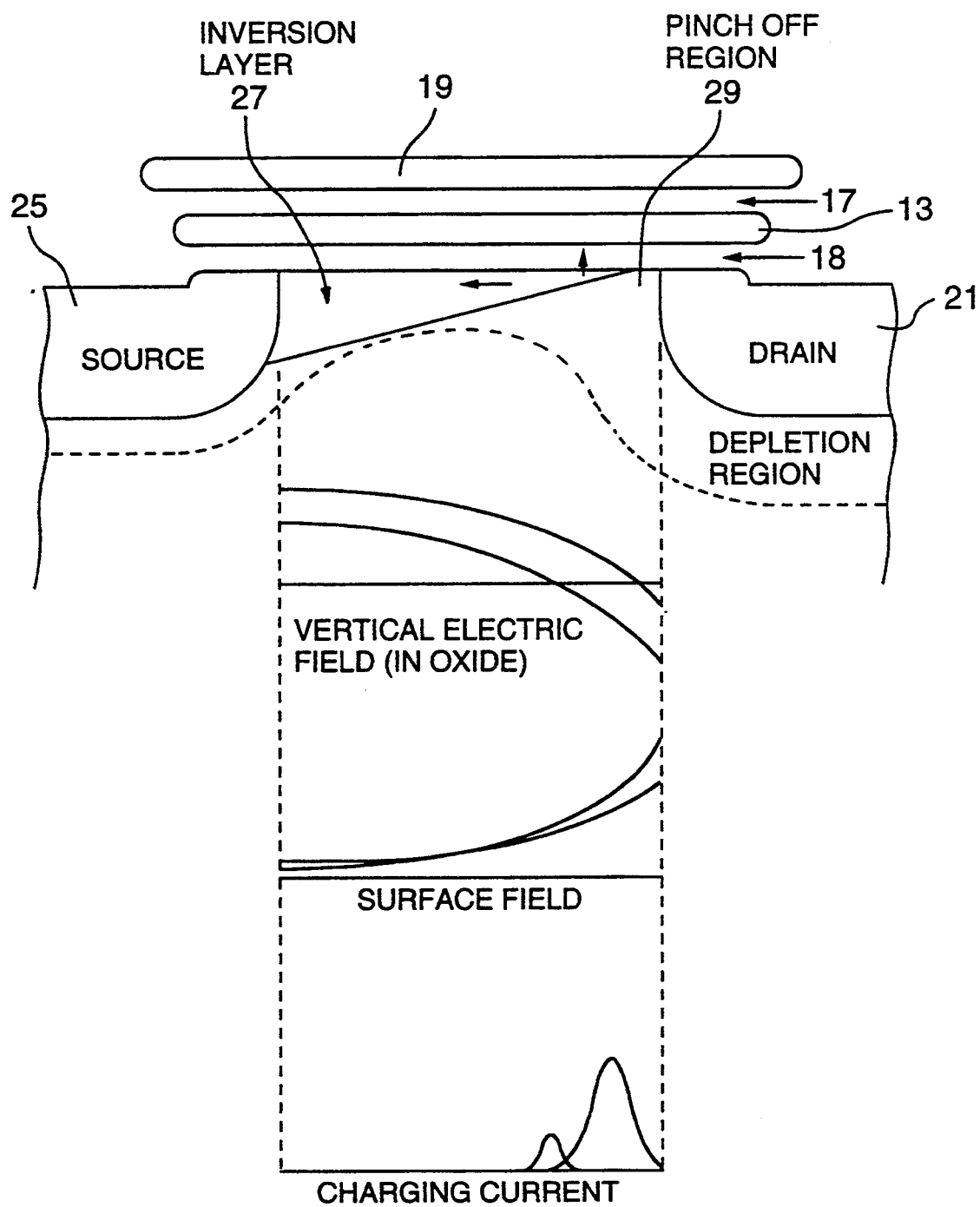
FIG. 6 is a further schematic cross section of the MOS transistor cell in FIGS. 3 and 4 showing electric field profiles with a positive floating gate potential.

Near the beginning of the injection process, the inversion layer 27 extends almost completely to the drain 21, and the field in the oxide is attractive except for a small portion very near the drain (see FIG. 6). Current begins to flow through the oxide 18 at the point where the electrons are their hottest and where the oxide field is most favorable. As the floating gate 13 charges up, the floating gate-to-source voltage drops and the drain pinch-off region 29 moves toward the source 25. The surface field near the drain 21 intensifies and more hot electrons are produced in the substrate 15.

However, as seen in FIG. 6, in the region where the electrons are their hottest, the oxide field is least favourable for injection and so the injected-electron current begins to subside. Thus, the electron injection process is self-limiting. The charging of the floating gate 13 reduces the number of electrons that can be accelerated in the high field region. As the floating gate 13 becomes fully charged, the oxide current is reduced almost to zero because the oxide field is repulsive to the electrons injected into the high-field region.

Cell erasure is accomplished by exposing the array to UV light. Photons are absorbed by electrons in the conduction and valence band of the polysilicon floating gate 13 at erasure UV wavelengths, most are absorbed within approximately 50 Å of the oxide interface. The excited electrons leave the polysilicon floating gate 13, enter the oxide 17, 18 and are swept away to the select gate 19 or substrate 15 by the local field. During erasure, the select gate 19, source 25, drain 21 and substrate 15 are all near ground potential.

With an n-type polysilicon floating gate 13, electrons can be excited from either the conduction band or the valance band to the oxide 17, 18. Excitation from the conduction band requires only 3.2 eV, while the barrier height from the valence band is 4.3 eV. Even for heavily doped n-type material there are many more electrons available from the valence band of the polysilicon floating gate than from the conduction band.

Figure 7:
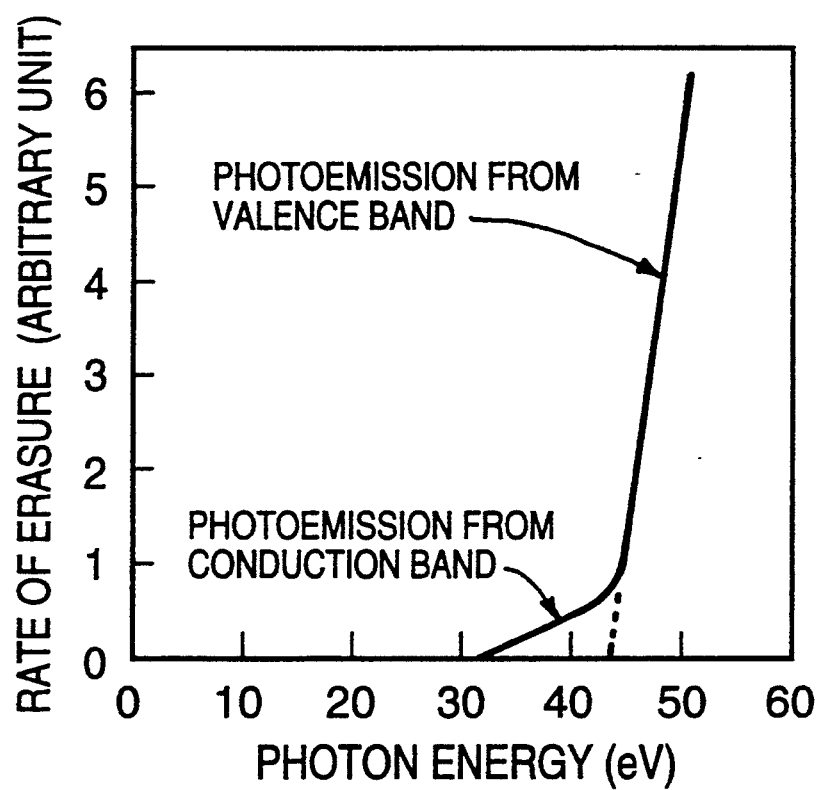
FIG. 7 is a graph relating rate of erasure of an EPROM cell to photon energy of UV light applied thereto.
Figure 8:
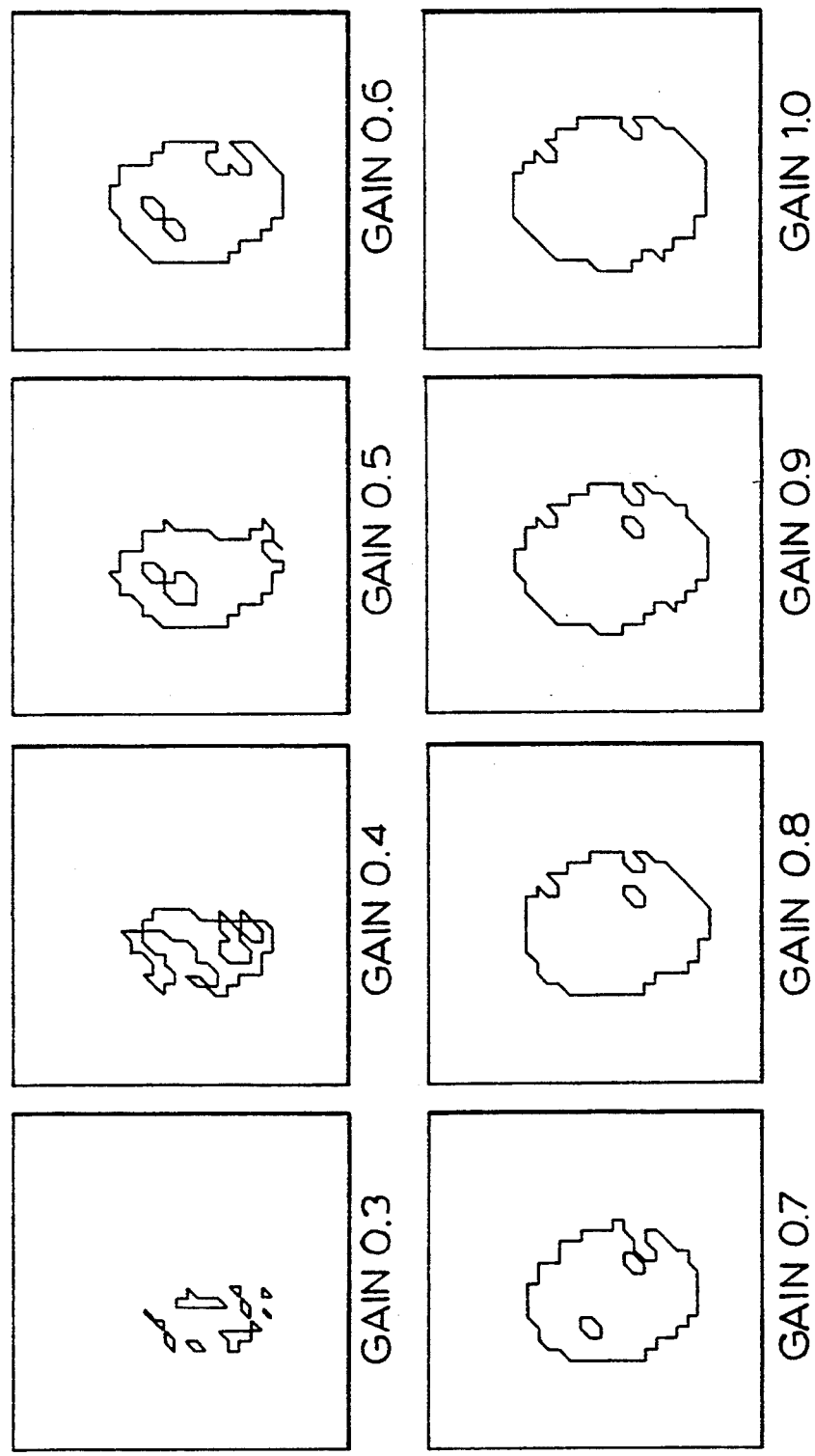
FIG. 8 shows a two-dimensional record of UV exposure of the artificial cornea according to the present invention at various depths of UV penetration.
Figure 9B:
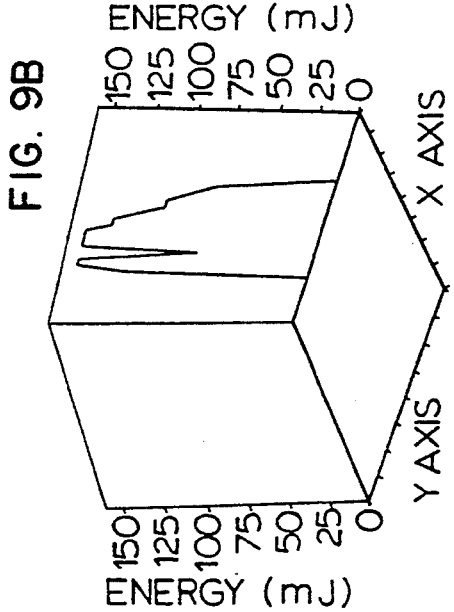
FIG. 9 shows two-dimensional and three-dimensional profile records of UV exposure of the artificial cornea according to the present invention.
Figure 9A:
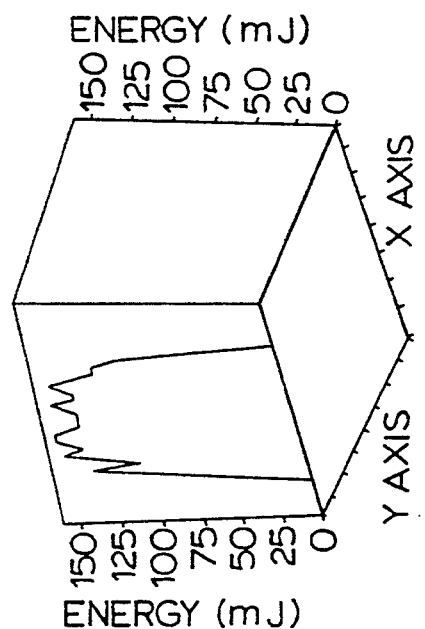
Figure 9D:
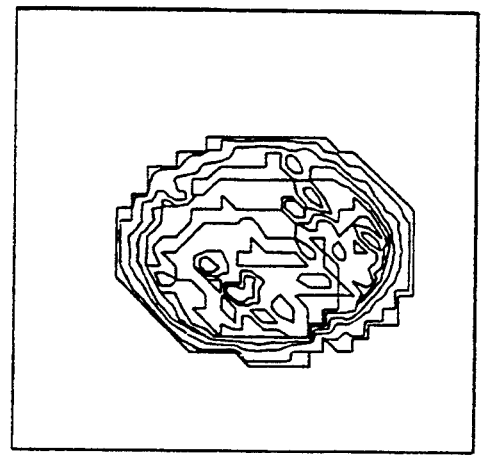
Figure 9C:
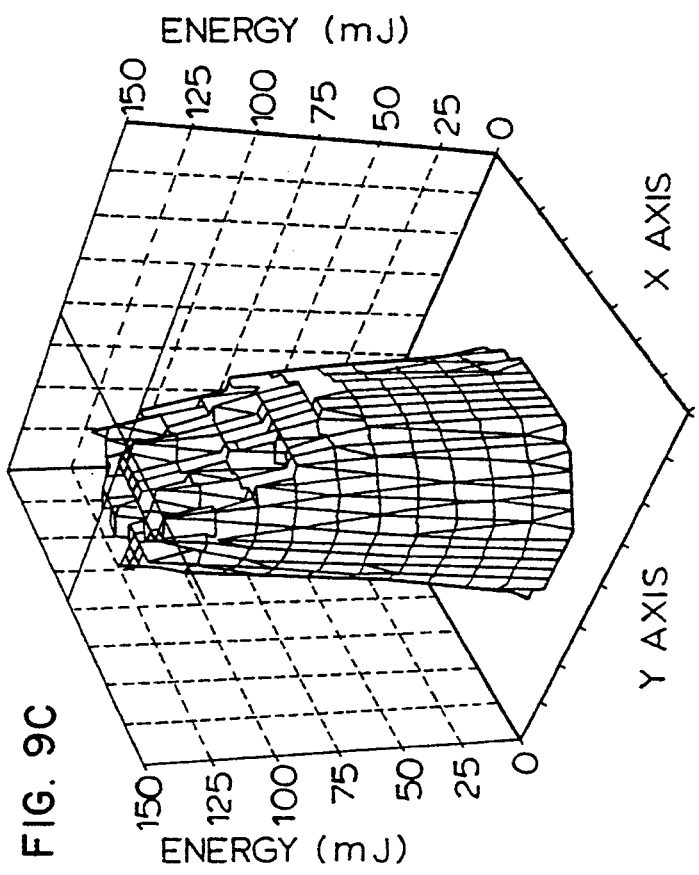

Quantum yield and the erasure rate per incident photon follows the square law dependence upon photon energy shown in FIG. 7. Two distinct threshold energies are apparent (see FIG. 7). The first, at 3.2 eV, is associated with the photo-excitation of electrons from the conduction band. Its slope is much shallower because of the lower density of electrons. The 4.3 eV threshold corresponds to the onset of photoemission from the valence band. The much steeper slope is indicative of much higher density of valence band electrons.

Tables 3 and 4 provide some data on the absorptivity (A) and the absorption coefficient (α) for various elemental and compound semiconductors at excimer laser wavelengths.

TABLE 3

Absorptivity calculated from (n,k) for selected semiconductors at 300° k.

| Material | Wavelength (nm) | | |
|---|---|---|---|
| | 308 nm | 248 nm | 196 nm |
| Ge | 0.44 | 0.35 | |
| Si | 0.41 | 0.33 | |
| GaP | 0.55 | 0.42 | |
| GaAs | 0.58 | 0.33 | |
| GaSb | 0.42 | 0.41 | |
| GeTe | 0.59 | 0.75 | 0.80 |
| InP | 0.62 | 0.39 | |
| InAs | 0.61 | 0.42 | |
| InSb | 0.39 | 0.46 | |
| PbS | 0.53 | 0.62 | 0.82 |
| PbSe | 0.29 | 0.50 | 0.77 |
| PbTe | 0.59 | 0.5 | 0.77 |
| SnTe | 0.49 | 0.66 | 0.75 |

TABLE 4

Absorption coefficient $\alpha(10^6 \text{ cm}^{-1})$ for various semiconductors at 300° K. and excimer wavelengths.

| Material | Wavelength (nm) | |
|---|---|---|
| | 308 nm | 248 nm |
| Ge | 1.35 | 1.62 |
| Si | 1.54 | 1.81 |
| GaP | 0.88 | 1.84 |
| GaAs | 0.78 | 2.07 |
| GaSb | 1.48 | 1.30 |
| InP | 0.70 | 1.77 |
| InAs | 0.73 | 1.46 |
| InSb | 1.50 | 1.24 |
| PbS | 0.92 | 0.82 |
| PbSe | 0.75 | 0.62 |
| PbTe | 0.80 | 0.67 |

Thus, according to the present preferred embodiment of the invention, an EPROM like array 32 is utilized for sensing and integrating UV exposure in an artificial cornea 31. The EPROM like array 32 is preferably provided with a variable erasing threshold. Prior to a UV laser keratectomy operation, all of the bits of the EPROM like array 32 must be set. When the UV laser 35 is focused on the active area of the artificial cornea 31, the UV radiation will cause localized erasures. By monitoring via computer 33, in real time, the locations of the erased bits and the number of pulses required to achieve the given erasure distribution on a focal spot, a three dimensional map of the energy distribution can be obtained (FIGS. 8 and 9). To achieve this, the delicate semiconductor surface of the EPROM like array 32 has to be protected from the intense laser light without affecting the erasure threshold sensitivity. Furthermore the sensitivity levels have to be matched, either electronically or through software, to the ablation characteristics of the cornea.

Figure 10:
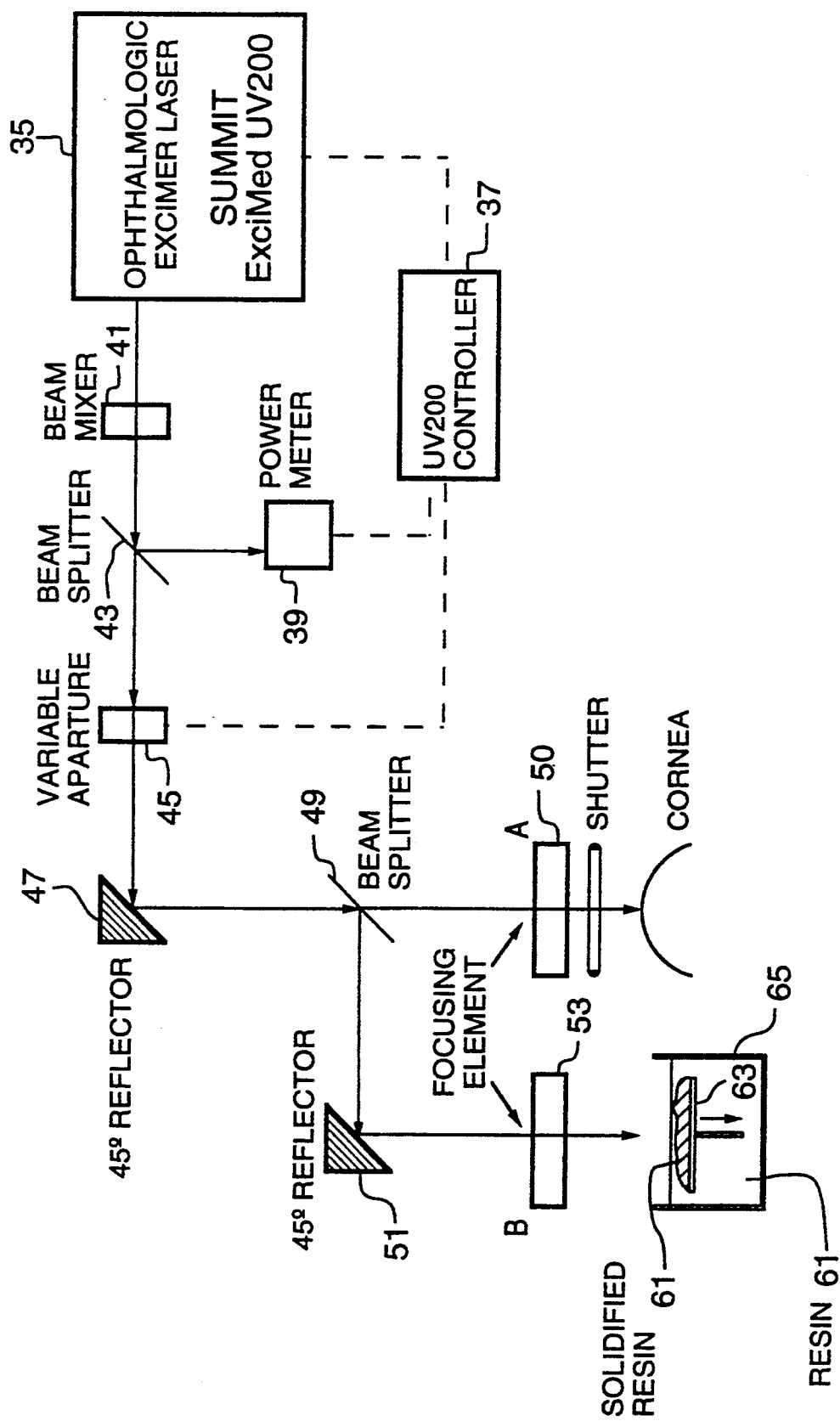
FIG. 10 is a block diagram of an artificial cornea and test system therefor, in accordance with a first alternative embodiment.
Figure 11:
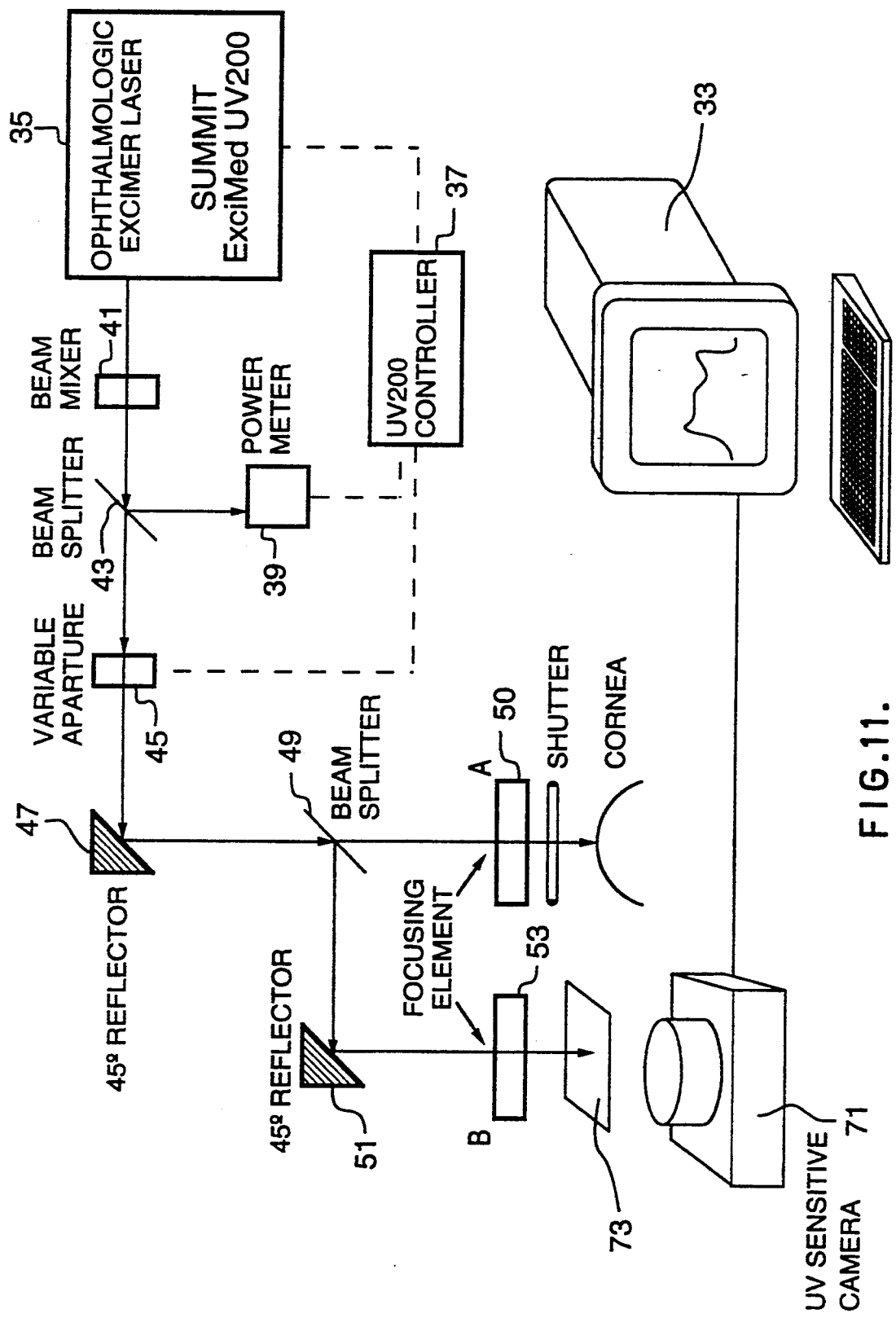
FIG. 11 is a block diagram of an artificial cornea and test system therefor, in accordance with a second alternative embodiment.
Figure 12:
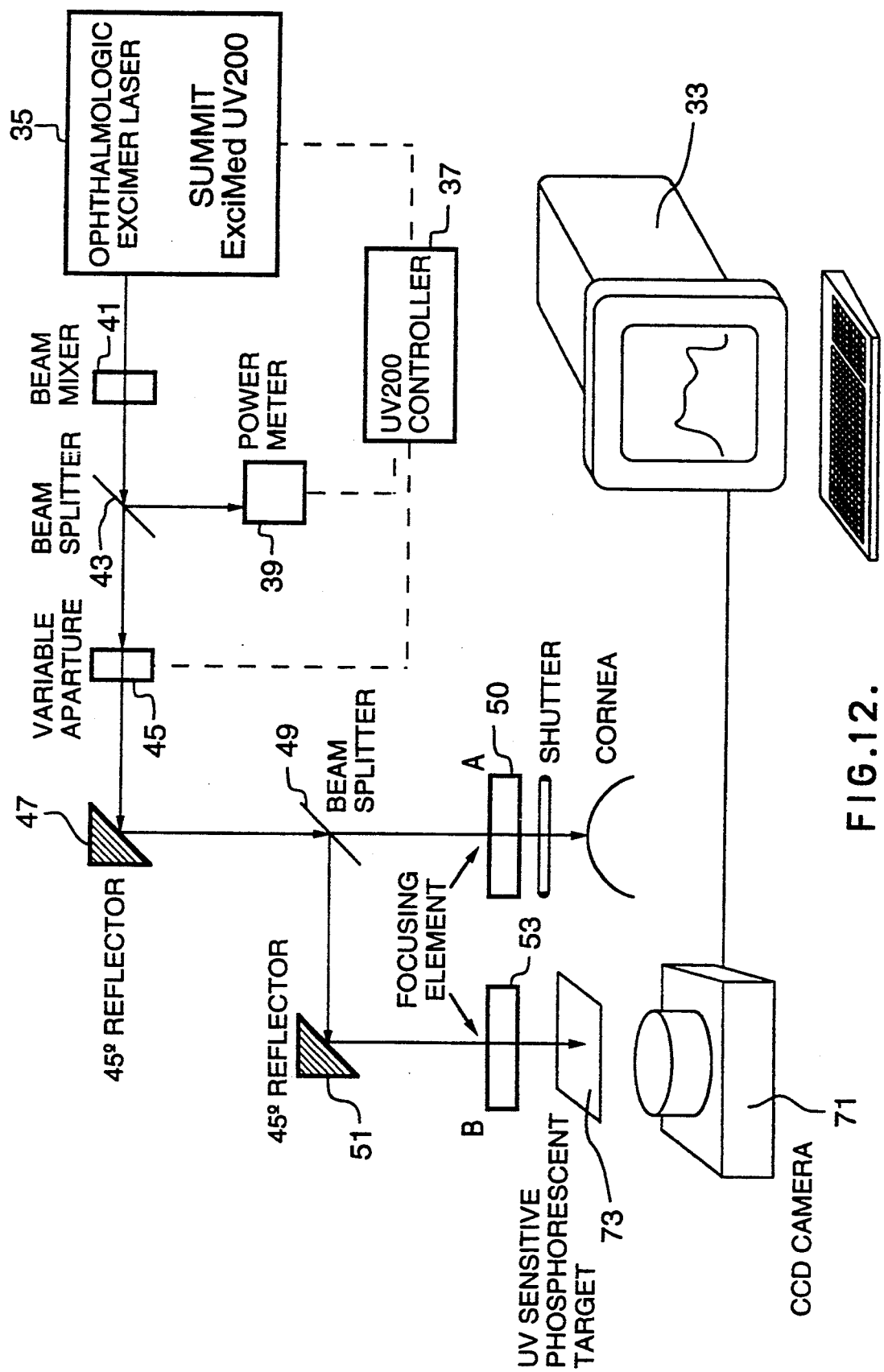
FIG. 12 is a block diagram of an artificial cornea and test system therefor, in accordance with a third alternative embodiment.

Other embodiments and variations of the invention are possible within the scope of the present description. For example, while the use of an EPROM like array 32 to detect and integrate UV radiation is preferred, other detection and integration methodologies may be utilized. FIG. 10 shows an artificial cornea in the form of a quantity of UV curable resin 61 supported on a vertically adjustable platform 63 within a cup 65. Portions of the resin 61 which are irradiated 61' become cured, the platform 63 is then lowered for irradiating the next layer of uncured resin 61. The curing profile then provides an indication of the radiation exposure of the artificial cornea. In this embodiment no computer is required. In the embodiments of FIGS. 11 and 12, a CCD camera 71 is used to detect UV exposure. In the embodiment of FIG. 11, a UV sensitive CCD camera is used to directly detect the UV exposure. In the embodiment of FIG. 12, the UV radiation is applied to a sheet of UV sensitive material 73 which phosphoresces in response to being irradiated. A standard CCD camera 71 is then used to detect the phosphorescencess thereby generated. The output of the camera 71 in the embodiments of FIGS. 11 and 12 is applied to computer 33 for further analysis and graphical display.

All such embodiments and variations are believed to be within the sphere and scope of the present invention as defined by the claims appended hereto.

We claim:

1. An artificial cornea for sensing and integrating UV radiation in real time, comprising:
    (a) an EPROM array adapted to be exposed to said UV radiation and having individual bits, said individual bits of said EPROM array being set prior to being exposed to said UV radiation, whereby in response to being exposed to said UV radiation predetermined ones of said individual bits are erased;
    (b) means for monitoring, in real time, the locations of said predetermined erased bits and in response forming a record of the energy distribution of said UV radiation across said EPROM array,
    said individual bits of said EPROM array are stored on a plurality of MOS transistors each comprising a substrate, a source region, a drain region, a select gate overlying a channel region of said substrate intermediate said drain region and said source region, an insulting layer intermediate said channel region and said select gate, and a floating gate buried in said insulating layer, whereby charge stored on said floating gate alters the threshold voltage of said MOS transistor as detected at said select gate.

2. The artificial cornea of claim 1 wherein said individual bits of said EPROM array are set prior to being exposed to said UV radiation by applying a voltage to said select gate and said drain region whereby hot electrons are injected into and thereby charge said floating gate from said channel.

3. The artificial cornea of claim 2 wherein said predetermined ones of said individual bits are erased via internal photoemission from the floating gate to the select gate and said substrate in response to being exposed to said UV radiation.

4. A method for real time sensing and integrating UV radiation of an artificial cornea, comprising:
    (a) storing charge on individual transistors of an EPROM array arranged in the shape of a human cornea;
    (b) exposing said EPROM array to said UV radiation, whereby said charge stored on predetermined ones of said individual transistors is erased; and
    (c) monitoring the locations of said predetermined ones of said individual transistors and in response forming a record of the energy distribution of said UV radiation across said EPROM array.

* * * * *

UNITED STATES PATENT AND TRADEMARK OFFICE
CERTIFICATE OF CORRECTION

PATENT NO.   : 5,387,106
DATED        : February 7, 1995
INVENTOR(S)  : Mackenzie et al.

It is certified that error appears in the above-indentified patent and that said Letters Patent is hereby corrected as shown below:

On the title page, column 2, line 16, "327" should be --337--.
    Column 1, line 53, "produces" should be --produced.
    Column 2, line 40, "in" should be --is--.
  Column 4, line 1, "Fig. 9 shows" should be --Figures 9A-9D show--.
    Column 4, line 32, "in" should be --is--.
    Column 5, line 23, "centre" should be --center--.
    Column 6, line 41, "artical" should be --artificial--.
    Column 7, line 15, "9" should be --9A-9D--.
    Column 7, line 20, "9" should be --9A-9D--.
    Column 9, line 54, "9" should be --9A-9D--.

Signed and Sealed this

Eleventh Day of July, 1995

*Attest:*

BRUCE LEHMAN

*Attesting Officer*    *Commissioner of Patents and Trademarks*